United States Patent
Rosenblatt et al.

(10) Patent No.: US 10,086,114 B2
(45) Date of Patent: Oct. 2, 2018

(54) ANTIMICROBIAL SOLUTIONS WITH ENHANCED STABILITY

(71) Applicant: Board of Regents, The University of Texas System, Austin, TX (US)

(72) Inventors: Joel Rosenblatt, Pottstown, PA (US); Issam Raad, Missouri City, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/344,113

(22) Filed: Nov. 4, 2016

(65) Prior Publication Data

US 2017/0151373 A1 Jun. 1, 2017

Related U.S. Application Data

(60) Provisional application No. 62/251,481, filed on Nov. 5, 2015.

(51) Int. Cl.

| | |
|---|---|
| *A61K 31/65* | (2006.01) |
| *A61K 31/505* | (2006.01) |
| *A01N 25/22* | (2006.01) |
| *A61L 29/16* | (2006.01) |
| *A01N 25/02* | (2006.01) |
| *A01N 45/00* | (2006.01) |
| *A61L 29/14* | (2006.01) |
| *A61J 1/20* | (2006.01) |
| *A61M 5/178* | (2006.01) |
| *A61M 25/00* | (2006.01) |
| *A01N 31/02* | (2006.01) |

(52) U.S. Cl.
CPC .............. *A61L 29/16* (2013.01); *A01N 25/02* (2013.01); *A01N 25/22* (2013.01); *A01N 31/02* (2013.01); *A01N 45/00* (2013.01); *A61J 1/2096* (2013.01); *A61K 31/505* (2013.01); *A61K 31/65* (2013.01); *A61L 29/143* (2013.01); *A61M 5/178* (2013.01); *A61M 25/00* (2013.01); *A61L 2300/404* (2013.01); *A61L 2300/406* (2013.01); *A61L 2300/45* (2013.01); *A61M 2025/0019* (2013.01)

(58) Field of Classification Search
None
See application file for complete search history.

(56) References Cited

U.S. PATENT DOCUMENTS

| | | | |
|---|---|---|---|
| 5,362,754 A | 11/1994 | Raad et al. | |
| 5,688,516 A | 11/1997 | Raad et al. | |
| 6,350,251 B1 | 2/2002 | Prosl et al. | |
| 7,601,731 B2 * | 10/2009 | Raad | A61K 45/06 514/279 |
| 8,541,472 B2 | 9/2013 | Kite et al. | |
| 2004/0110841 A1 | 6/2004 | Kite et al. | |

FOREIGN PATENT DOCUMENTS

| | | |
|---|---|---|
| EP | 1245247 | 10/2002 |
| WO | WO 2012-167368 | 12/2012 |

OTHER PUBLICATIONS

"Minocin IV," Instructions for use, Rempex Pharmaceuticals, Inc., 2014.
"Minocycline hydrochloride," *Pharmacopeial Forum*, 28(3):770, located at http://www.pharmacopeia.cn/v29240/usp29nf24s0_m54170.html, downloaded 2017.
Kluger et al., "A meta-analysis of the risk of intravascular device-related blood stream infection based on 223 published prospective studies," In: Interscience Conference on Antimicrobial Agents and Chemotherapy (ICAAC) Abstracts of the 39th Meeting, 514, 1999.
Maki et al., In: Hospital Infections, Bennett and Brachman, eds. Lippincott-Raven, Philadelphia, PA., pp. 689-694, 1998.
PCT International Search Report and Written Opinion issued in International Application No. PCT/US2016/060571, dated Feb. 23, 2017.
Raad et al., "Chelator-based catheter lock solutions in eradicating organisms in biofilm," *Antimicrobial Agents and Chemotherapy*, 57(1):586-588, 2013.
Raad et al., "Efficacy of minocycline and EDTA lock solution in preventing catheter-related bacteremia, septic phlebitis, and endocarditis in rabbits," *Antimicrob. Agents Chemother.*, 46(2):327-332, 2002.
Raad et al., "Intravascular catheter-related infections: new horizons and recent advances," *Arch. Intern. Med.*, 162:871-878, 2002.
Raad et al., "Optimal antimicrobial catheter lock solution, using different combinations of minocycline, EDTA, and 25-percent ethanol, rapidly eradicates organisms embedded in biofilm,"*Antimicrobial Agents and Chemotherapy*, 51(1):78-83, 2007.
Raad et al., "Ultrastructural analysis of indwelling vascular catheters: a quantitative relationship between luminal colonization and duration of placement," *J. Infect. Dis.*, 168:400-407, 1993.
Sherertz et al., "In vitro efficacy of minocyline (M)/EDTA (MEDTA) as a catheter lock solution," Shea Merck Healthcare Epidemiology Search Abstracts, 2002.
Venkatesh et al., "Novel synergistic antibiofilm combinations for salvage of infected catheters," *Journal of Medical Microbiology*, 58(7):936-944, 2009.

* cited by examiner

Primary Examiner — Brian J Davis
(74) Attorney, Agent, or Firm — Parker Highlander PLLC

(57) ABSTRACT

Provided are antimicrobial solutions, including catheter lock solutions. In some embodiments, the solution contains an antibiotic (e.g., minocycline or trimethoprim), EDTA, and an alcohol (e.g., ethanol), wherein the pH of the solution is adjusted to about 6-8 to reduce precipitation. Methods of using the solutions and kits are also provided.

30 Claims, No Drawings

ANTIMICROBIAL SOLUTIONS WITH ENHANCED STABILITY

This application claims the benefit of U.S. Provisional Patent Application No. 62/251,481, filed Nov. 5, 2015, the entirety of which is incorporated herein by reference.

BACKGROUND OF THE INVENTION

1. Field of the Invention

The present invention relates generally to the field of molecular biology and medicine. More particularly, it concerns antimicrobial compositions such as, e.g., antimicrobial catheter lock solutions.

2. Description of Related Art

Microbial contamination of medical devices, such as catheters, continues to present a significant clinical problem. Medical devices, such as vascular catheters, have improved the quality of medical care. However, infections resulting from the colonization of organisms embedded in biofilm are the most frequent complication associated with the use of these and other indwelling and/or prosthetic devices. In fact, infections are the most serious complications associated with indwelling central venous catheters (CVCs) (Maki et al., 1998). It is estimated that more than 200,000 catheter-related bloodstream infections (CRBSI) occur annually in the United States alone (Kluger et al., 1999). *Staphylococcus epidermidis, Staphylococcus aureus* and *Candida* species are the leading organisms causing CRBSI (Maki et al., 1998; Raad et al., 2002).

While there is a risk of bacterial colonization of a catheter, use of a catheter lock solution can allow continued use of a catheter, and removal of the catheter from a patient is often problematic in many clinical situations. Antimicrobial catheter lock solutions can provide salvage of colonized vascular catheters in the setting of blood stream infections. For many critically ill patients, removal or exchange of a vascular catheter in the setting of blood stream infection is a poor option. There is a risk of vessel irritation or rupture as well as bleeding. The risk of bleeding is particularly significant in patients with underlying coagulopathies such as cancer patients. There is also a risk of cardiac taponade as well as cost associated with radiologic imaging to verify tip position of the replacement catheter. Antimicrobial catheter lock solutions can also serve the valuable function of preventing a catheter from becoming a source of blood stream pathogens in the setting of blood stream infection.

Nonetheless, intralumenal colonization is the major source for the migration of organisms leading to bloodstream infections in long-term silicone catheters (Raad et al., 1993). While progress has been made in reducing bacterial infiltration of medical devices or indwelling medical devices, infections resulting from bacterial colonization of medical devices continues. Clearly, there is a need for new and improved antimicrobial solutions, such as improved antimicrobial catheter lock solutions.

SUMMARY OF THE INVENTION

The present invention overcomes limitations in the prior art by providing, in certain aspects, improved antimicrobial compositions (e.g., improved catheter lock solutions) that display improved stability and storage. The present invention is based, in part, on the observation that some antimicrobial compositions can result in an undesirable precipitation of antimicrobial components from the solution, thus limiting utility of the solution. In some aspects, improved antimicrobial solutions are provided herein that exhibit reduced precipitation of components in solution and improved stability.

As shown in the below examples, the inventors have observed that inclusion of both EDTA and an alcohol in an antimicrobial solution with an antibiotic can result in an undesirable precipitation (e.g., of the EDTA and/or antibiotic) from the solution, which may reduce the antimicrobial properties of the antimicrobial solution. Further, this precipitate may produce undesirable consequences in a catheter lock or flush solution since, e.g., the precipitate may clog catheter lumens or create emboli.

Simply reducing the concentration of EDTA in the antimicrobial solution might be expected to reduce the precipitation of EDTA; however, reducing the concentration of EDTA could also reduce the antimicrobial properties of the resulting antimicrobial composition. In some aspects, the present invention is based, in part, on the surprising discovery that antimicrobial solutions comprising both EDTA and an alcohol (e.g., ethanol), when adjusted to about pH 6-8, can result in compositions that display in little or no undesirable precipitation of the EDTA over extended periods of time (e.g., for at least about 24 hours, at least about 48 hours, or at least 72 hours after mixture with an antibiotic such as minocycline). To the knowledge of the inventors, neither this problem nor this solution is described in the prior art.

As shown in the below examples, while using of the triple combination minocycline/EDTA/Ethanol (M/EDTA/Ethanol) as described in U.S. Pat. No. 7,601,731, the inventors observed that a precipitate began to form within 24 hours of preparing this triple combination (M/EDTA/Ethanol) lock solution. In clinical usage, in some situations it is impossible or undesirable to immediately use all the prepared lock solution, e.g., when the lumens of a catheter are in service for administering medication, hydration, nutrition or diagnostics. In some cases, the availability of individuals trained to mix the lock may be limited, creating a need for storage. Furthermore, due of the cost of Minocycline, may be economically preferable to store unused lock solutions for limited durations rather than to discard them. As shown in the below examples, antimicrobial solutions observed to provide for at least about 72 hours of stable storage of prepared lock solution prior to use. A stable (e.g., stable for at least 72 hours) lock solution comprising M/EDTA/Ethanol can be prepared, e.g., when a fourth component is added to adjust the pH to the range of about 6-8. Several stable four component/EDTA/Ethanol lock solutions are described. Kit designs for salvage of infected catheters via antimicrobial lock therapy with the stable lock solution are also provided. In some embodiments, the antimicrobial solution or catheter lock solution may contain:

(i) Alcohol+Antimicrobial agent+acidic EDTA (such as disodium EDTA)+sufficient base (such as sodium or potassium hydroxide) to adjust pH to 6-8;

(ii) Alcohol+antimicrobial agent+basic EDTA (such as tetrasodium EDTA)+sufficient acid (such as hydrochloric or acetic acid) to neutralize pH to 6-8; or (iii) Alcohol+antimicrobial agent+acidic EDTA (such disodium EDTA)+basic EDTA (such as tetrasodium EDTA) in proportion to attain pH 6-8. In some embodiments, a mixture of acidic and basic EDTAs is sometimes sold as trisodium EDTA and can have a pH of 6.5-7.5 depending on the ratio, and may be used in the antimicrobial solution or catheter lock solution.

As aspect of the present invention relates to a pharmaceutically acceptable antimicrobial solution comprising: (i) a $C_{1-4}$ alcohol; (ii) an EDTA; and (iii) an antibiotic; wherein said solution has a pH of about 6-8, and wherein said solution comprises a pharmaceutically acceptable excipient or diluent. In some embodiments the antibiotic is trimethoprim or minocycline. In some embodiments, the $C_{1-4}$ alcohol is ethanol, isopropanol, methanol, or butanol. In some embodiments, the $C_{1-4}$ alcohol is ethanol. The $C_{1-4}$ alcohol may be present in the solution at a concentration of about 10-40%. In some embodiments, the $C_{1-4}$ alcohol is present in the solution at a concentration of about 10-30%, 10%, 15%, 20%, 25%, 30%, 35%, 40%, or any range derivable therein. The $C_{1-4}$ alcohol may be ethanol. In some embodiments, the solution comprises about 1-5%, 1.5-5% 1-3.5%, 1-3%, or about 3% EDTA. The solution may comprise about 1, 1.5, 2, 2.5, 3, 3.5, 4, 4.5, or 5% EDTA, or any range derivable therein. In some embodiments, the EDTA is EDTA free acid, EDTA 2Na, EDTA 3Na, EDTA 4Na, EDTA 2K, EDTA 2Li, EDTA $2NH_4$, EDTA 3K, Ba(II)-EDTA, Ca(II)-EDTA, Co(II)-EDTA, Cu(II)-EDTA, Dy(III)-EDTA, Eu(III)-EDTA, Fe(III)-EDTA, In(III-EDTA, La(III)-EDTA, EDTA-OH, or Methyl-EDTA. The solution may comprise about 0.05-0.2% antibiotic. In some embodiments, the solution comprises about 0.1% minocycline, about 3% EDTA, and about 25% ethanol. In some embodiments, the EDTA is an acidic EDTA, and wherein the solution further comprises a base. In some embodiments, the acidic EDTA is EDTA free acid, EDTA 2Na, EDTA 2K, EDTA diammonium, or a diacid of EDTA. In some embodiments, the base is sodium hydroxide, potassium hydroxide, ammonia, an amine, or urea. In some embodiments, the EDTA is a basic EDTA, and wherein the solution further comprises an acid. In some embodiments, the basic EDTA is EDTA 4Na, EDTA 4K, or tetra ammonium EDTA. The acid may be hydrochloric acid or acetic acid. In some embodiments, the solution comprises both an acidic EDTA and a basic EDTA. The acidic EDTA may be EDTA free acid, EDTA 2Na, dipotassium EDTA, or diammonium EDTA; and wherein the basic EDTA is EDTA 4Na, tetra potassium EDTA (EDTA 4K), or tetra ammonium EDTA. The solution may comprise a pharmaceutically acceptable saline diluent or a pharmaceutically acceptable diluent. The solution has a pH of about 6.5-7.5, of about 7-7.4, or 6.5, 6.6, 6.7, 6.8, 6.9, 7.0, 7.1, 7.2, 7.3, 7.4, 7.5, or any range derivable therein. The solution may further comprise polyethylene glycol. In some embodiments, the solution is further defined as a catheter lock solution. In some embodiments, the fraction of EDTA in the tetravalent form is between about 0.1 and about 0.000001, preferably between about 0.05 and about 0.000005, or more preferably between about 0.01 and about 0.00001, or any range derivable therein (e.g., about 0.0042-0.000018, about 0.001-0.0001, about 0.0025-0.000025, about 0.0025-0.000075, etc.).

Another aspect of the present invention relates to a syringe, comprising a unit dose of a pharmacologically effective amount of a solution of the present invention (e.g., an antimicrobial solution or catheter lock solution as described herein) or as described above.

Yet another aspect of the present invention relates to a vial, comprising a unit dose of a pharmacologically effective amount of a solution of the present invention (e.g., an antimicrobial solution or catheter lock solution as described herein) or as described above.

Another aspect of the present invention relates to a medical device locking solution comprising or consisting of a solution of the present invention (e.g., an antimicrobial solution or catheter lock solution as described herein) or as described above.

Yet another aspect of the present invention relates to a kit comprising: (i) an antibiotic in a first container; (ii) a solution containing an EDTA and an alcohol at a pH of about 6-8 in in a second container; (iii) a suitable connector for mixing the antibiotic and the solution; and (iv) a suitable syringe or container for administering the mixed solution to a catheter. In some embodiments, one or more labels or removable extension-line tags is attached to the catheter. The tags may be symmetric peel-off tags comprising adhesive on one side and optionally having pre-perforated lines (e.g., on about the mid-section of the tags). The mixed solution may be a solution of the present invention (e.g., an antimicrobial solution or a catheter lock solution). The antibiotic may be lyophilized. In some embodiments, the alcohol is ethanol. In some embodiments, the first container is a vial or syringe, and wherein the second container is a vial or syringe. In some embodiments, the antibiotic is a lyophilized antibiotic, and wherein the first container and the second container are each a vial or syringe.

Yet another aspect of the present invention relates to a method of flushing or locking a catheter in a subject, comprising administering the solution of a solution of the present invention. The catheter may be an intravascular catheter, a urinary catheter, a brain catheter, a nephrostomy tube, or a drain or drainage catheter. In some embodiments, the subject is a human.

Another aspect of the present invention relates to a solution for use in flushing or locking a catheter in a subject, wherein the solution is a solution the present invention (e.g., an antimicrobial solution as described above or herein). The catheter may be an intravascular catheter, a urinary catheter, a brain catheter, a nephrostomy tube, or a drain or drainage catheter. In some embodiments, the subject is a human.

A variety of EDTA chelator molecules may be used with the present invention. In some embodiments, the composition may comprise an additional chelator molecule. The EDTA or chelator may be, e.g., EDTA free acid, EDTA 2Na, EDTA 3Na, EDTA 4Na, EDTA 2K, EDTA 2Li, EDTA $2NH_4$, EDTA 3K, Ba(II)-EDTA, Ca(II)-EDTA, Co(II)-EDTA Cu(II)-EDTA, Dy(III)-EDTA, Eu(III)-EDTA, Fe(III)-EDTA, In(III-EDTA, La(III)-EDTA, CyDTA, DHEG, diethylenetriamine penta acetic acid (DTPA), DTPA-OH, EDDA, EDDP, EDDPO, EDTA-OH, EDTPO, EGTA, HBED, HDTA, HIDA, IDA, Methyl-EDTA, NTA, NTP, NTPO, O-Bistren, TTHA, EGTA, DMSA, deferoxamine, dimercaprol, zinc citrate, a combination of bismuth and citrate, penicillamine, succimer or Etidronate. It is contemplated that a chelator that binds barium, calcium, cerium, cobalt, copper, iron, magnesium, manganese, nickel, strontium, or zinc may be included in various embodiments of the present invention.

Trisodium EDTA is not as commonly available as the other salts and has a pH of 9.5 (e.g., Dissolvine NA3-36 AkzoNobel Industrial Chemicals Amersfoort, Netherlands; CAS 150-38-9). Trisodium EDTA is sometimes sold as a blend of di- and tetra-sodium EDTAs which can have pH depending on the blend ratio. This however is not a single EDTA salt. Some Trisodium EDTAs for cell culture applications are treated with diethyl pyrocarbonate (DEPC), which lowers the pH to 8 (Santa Cruz Biotechnology, Dallas, Tex.; Millipore, Billerica, Mass.). The DEPC adjusted Trisodium EDTA is not a pure, single salt form of EDTA and because of the additive would require extensive safety testing for blood contact in humans. EDTA is a tetra-acid. The different anions coexist in solution with fractional presence dependent on solution pH. Between pH 6 and 8 the predominant fractions are di and trivalent, but a small fraction of tetra valent is also present. Harris (2010) reports that at 20 degrees Celsius and 0.1 Molar concentration that the fraction of EDTA that is tetravalent at pH 8 is about 0.0042 and the fraction that is tetravalent at pH 6 is about 0.000018 ($1.8 \times 10^{-5}$). Solutions of EDTA with the desired final pH can be prepared by blending salts with different valences or by adjusting the pH to the desired range by addition of acid or base; however accomplished, the fraction of tetravalent EDTA in the solution (as compared to the other forms of EDTA, i.e., as compared to the mono-, di-, and tri-valent forms of EDTA) may preferably be between about 0.1 and about 0.000001, more preferably between about 0.05 and about 0.000005, and even more preferably between about 0.01 and about 0.00001, or any range derivable therein (e.g., about 0.0042-0.000018, about 0.001-0.0001, etc.).

A "$C_{1-4}$ alcohol", as used herein, refers to a small-chain alcohol having 1-4 carbons. In some embodiments the $C_{1-4}$ alcohol is methanol, ethanol, butanol (n-butanol), isopropanol, n-propanol, 2-butanol, tert-butanol or isobutanol. In some embodiments, the $C_{1-4}$ alcohol (e.g., ethanol) is present in an antimicrobial solution of the present invention at a concentration of less than about 30%, more preferably less than about 28%. In some embodiments, the $C_{1-4}$ alcohol (e.g., ethanol) is present in an antimicrobial solution of the present invention at a concentration of about 1-30%, 2.5-25%, 5-25%, 5-15%, 10-15%, 5-10%, or about 1, 2, 3, 4, 5, 6, 7, 8, 9, 10, 11, 12, 13, 14, 15, 16, 17, 18, 19, 20, 21, 23, 24, 25%, or any range derivable therein.

A variety of antibiotics may be used with the present invention. In some embodiments, the antibiotic is trimethoprim and/or minocycline. In various embodiments, one or more additional antimicrobial agent (e.g., an alcohol, EDTA, and trimethoprim and/or minocycline, optionally in combination with one or more antimicrobial agent) may be included in an antimicrobial solution or composition of the present invention. For example, one or more antibiotic agent(s) may be included in an antimicrobial solution of the present invention (e.g., a catheter lock solution), such as, e.g., aminoglycosides, beta lactams, quinolones or fluoroquinolones, macrolides, sulfonamides, sulfamethaxozoles, tetracyclines, streptogramins, oxazolidinones (such as linezolid), clindamycins, lincomycins, rifamycins, glycopeptides, polymxins, lipo-peptide antibiotics, as well as pharmacologically acceptable sodium salts, pharmacologically acceptable calcium salts, pharmacologically acceptable potassium salts, lipid formulations, derivatives and/or analogs of the above. The antibiotic may be a member of the penicillin group of antibiotics such as, e.g., amoxicillin, ampicillin, benzathine penicillin G, carbenicillin, cloxacillin, dicloxacillin, piperacillin, or ticarcillin, etc. Examples of cephalosporins include ceftiofur, ceftiofur sodium, cefazolin, cefaclor, ceftibuten, ceftizoxime, cefoperazone, cefuroxime, cefprozil, ceftazidime, cefotaxime, cefadroxil, cephalexin, cefamandole, cefepime, cefdinir, cefriaxone, cefixime, cefpodoximeproxetil, cephapirin, cefoxitin, cefotetan etc. Examples of beta lactamase inhibitors include clavulanate, sulbactam, or tazobactam. The antibiotic may be a macrolide such as, e.g., erythromycin, azithromycin, or clarithromycin. Examples of quinolones and fluoroquinolones that may be used include nalidixic acid, cinoxacin, trovafloxacin, ofloxacin, levofloxacin, grepafloxacin, trovafloxacin, sparfloxacin, norfloxacin, ciprofloxacin, moxifloxacin and gatifloxacin. Examples of sulphonamides that may be used include mafenide, sulfisoxazole, sulfamethoxazole, and sulfadiazine. The streptogramin class of antibacterial agents is exemplified by quinupristin, dalfopristin or the combination of two streptogramins. Drugs of the rifamycin class typically inhibit DNA-dependent RNA polymerase, leading to suppression of RNA synthesis and have a very broad spectrum of activity against most gram-positive and gram-negative bacteria including *Pseudomonas aeruginosa* and *Mycobacterium* species. An exemplary rifamycin is rifampicin. Other antibacterial drugs are glycopeptides such as vancomycin, teicoplanin and derivatives thereof. Yet other antibacterial drugs are the polymyxins which are exemplified by colistin. In addition to these several other antibacterial agents such as prestinomycin, chloramphenicol, trimethoprim, fusidic acid, metronidazole, bacitracin, spectinomycin, nitrofurantion, daptomycin or other leptopeptides, oritavancin, dalbavancin, ramoplamin, ketolide etc. may be used in preparing the compositions described herein.

In some embodiments, an antimicrobial solution (e.g., a catheter lock solution) of the present invention may include member of the tetracycline group of antibiotics such as tigecycline, minocycline, doxycycline, or demeclocycline and/or analogs such as anhydrotetracycline, chlorotetracycline, or epioxytetracycline. In some embodiments, it is anticipated that a derivative of minocycline may be substituted for minocycline in various antimicrobial solutions or catheter lock solutions as described herein. In some embodiments, antimicrobial solutions or catheter lock solutions as described herein may include one or more additional antiviral agents and/or antifungal agents.

In other embodiments of the invention, the antimicrobial agent is an antiseptic agent. Several antiseptic agents are known in the art and these include a taurinamide derivative, a phenol, a quaternary ammonium surfactant, a chlorine-containing agent, a quinaldinium, a lactone, a dye, a thiosemicarbazone, a quinone, a carbamate, urea, salicylamide, carbanilide, a guanide, an amidine, an imidazoline biocide, acetic acid, benzoic acid, sorbic acid, propionic acid, boric acid, dehydroacetic acid, sulfurous acid, vanillic acid, esters of p-hydroxybenzoic acid, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, N(5-nitro-2-furfurylidene)-1-amino-hydantoin, 5-nitro-2-furaldehyde semicarbazone, 3,4,4'-trichlorocarbanilide, 3,4',5-tribromosalicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver sulfadiazine, or silver nitrate.

In some embodiments, the antimicrobial solution or composition may comprise a basic reagent and/or a dye. The basic reagent may be a guanidium compound, a biguanide, a bipyridine, a phenoxide antiseptic, an alkyl oxide, an aryl oxide, a thiol, a halide, an aliphatic amine, or an aromatic amine. In some specific aspects, the basic reagent is a guanidium compound. Non-limiting examples of guanidium compounds include chlorhexidine, alexidine, hexamidine. In other specific embodiments, the basic reagent is a bipyridine. One example of a bipyridine is octenidine. In yet other aspects, the basic reagent is a phenoxide antiseptic.

The dye may be a triarylmethane dye, a monoazo dye, a diazo dye, an indigoid dye, a xanthene dye, an anthraquinone dye, a quinoline dye, an FD&C dye. Non-limiting examples of triarylmethane dye include gentian violet, crystal violet, ethyl violet, or brilliant green. Exemplary monoazo dyes include FD&C Yellow No. 5, or FD&C Yellow No. 6. Other non-limiting examples of FD&C dye include Blue No. 1 or Green No. 3. One non-limiting example of diazo dyes is D&C Red No. 17. An example of an indigoid dye is FD&C Blue No. 2. An example of a xanthene dye is FD&C Red No. 3; of an anthraquinone dye is D&C Green No. 6; and of an quinoline dye is D&C Yellow No. 1.

In some embodiments, an antimicrobial may contain one or more antiseptics. For examples, the antiseptic may be a phenoxide antiseptic (e.g., clofoctol, chloroxylenol or triclosan), gendine, genlenol, genlosan, or genfoctol.

Antimicrobial compositions and methods described herein can be used to reduce microbial agents (e.g., bacteria) from the surface of a medical device such as, e.g., a catheter, a drain, an endotracheal tube, a nephrostomy tube, a ventricular catheter or shunt, a biliary stent, an orthopedic device, a prosthetic valve, a medical implant, dental devices or dental implants, cardiac assist devices, vascular grafts, tracheostomy, ventriclulostomy devices, or intrathecal devices. In some aspects, the catheter is an indwelling catheter such as a central venous catheter, a peripheral intravenous catheter, an arterial catheter, a Swan-Ganz catheter, a hemodialysis catheter, a urinary catheter, a peritoneal catheter, an umbilical catheter, a percutaneous nontunneled silicone catheter, a cuffed tunneled central venous catheter or a subcutaneous central venous port. In some embodiments, the medical device is an endotracheal tube, a vascular catheter, a urinary catheter, a nephrostomy tube, a biliary stent, a peritoneal catheter, an epidural catheter, a central nervous system catheter, an intracranial catheter, an intraspinal catheter, an epidural catheter, an orthopedic device, a prosthetic valve, or a medical implant. The catheter may be a vascular catheter such as, e.g., a central venous catheter, an arterial line, a pulmonary artery catheter, and a peripheral venous catheter, an intraarterial catheter, or intravenous (i.v.) tubing.

In some embodiments, a pharmaceutical composition or catheter lock solution of the present invention may comprise a pharmaceutically acceptable excipient. The phrases "pharmaceutically acceptable" and "pharmacologically acceptable" refer to molecular entities and compositions that do not produce an adverse, allergic or other untoward reaction when administered to an animal, such as, for example, a human, as appropriate. The preparation of an pharmaceutical composition that contains an antimicrobial solution (e.g., a catheter lock solution) of the present invention and an additional active ingredient will be known to those of skill in the art in light of the present disclosure, as exemplified by *Remington: The Science and Practice of Pharmacy, 21st Ed.*, Lippincott Williams and Wilkins, 2005, incorporated herein by reference. Moreover, for animal (e.g., human) administration, it will be understood that preparations should typically meet sterility, pyrogenicity, general safety and purity standards as required by FDA Office of Biological Standards. In some embodiments, an antimicrobial solution or catheter lock solution may comprise one or more ingredient as described in U.S. Pat. Nos. 7,601,731, 5,362,754, and 5,688,516, which are incorporated by reference in their entirety without disclaimer. In some embodiments, an antimicrobial composition or catheter lock solution of the present invention may comprise one or more additional antiviral or antifungal agent.

Other than reduction/eradication of microbes in medical devices, the flush solutions of the present invention are also useful in the eradication of the surfaces of other surfaces that microbes can grow on such as pipes, pipelines (e.g., an oil or water pipeline), ice machines, etc. Fluid pipelines, such as oil and water pipelines, are often obstructed by lumenal biofilm that is produced by microorganisms that colonize the internal surface of these pipelines. In these embodiments, higher concentrations of an alcohol may be used (e.g., 1-80% or higher). In some embodiments, an antimicrobial composition of the present invention may be used for oral hygiene, e.g., as a mouthwash or for topical (skin) disinfection. In some embodiments, an antimicrobial solution as described herein may be used to clean or disinfect a surface, or may be included on a wipe.

In some aspects, kit designs are provided that may reduce errors in salvaging a catheter in a patient experiencing infection symptoms. This can include salvage of vascular catheters in patients experiencing bacteremia. This is particularly a problem with multilumen catheters, where some lumens need to remain in use while others can be locked for a required disinfecting interval. Following disinfection of the locked lumen(s), the lumens can be rotated where the disinfected lumen becomes used for infusion and the lumen being previously used for disinfection becomes locked. With as many as 5 or more lumens, it can become confusing to keep track of which lumens were treated and which were in use. To overcome this problem, a user-ready kit supplied with Minocycline in dry form (powder or lyophilized) and pH adjusted EDTA-Ethanol as a liquid, may include removable extension-line tags which can be preprinted or filled in by the clinician denoting the time that lock therapy was initiated and the tag may indicate how long that lumen should be left locked, so as not to inadvertently terminate lock therapy before that lumen could be disinfected. Also lock therapy completed tags may also be included. Spaces for writing in the dates and color coding of the tags can be used. Symmetric peel-off tags with adhesive on one side which have pre-perforated lines down their mid-sections may be used for this purpose. In some embodiments, these tags can be folded on themselves such that the pre-perforated line contacts and is axially parallel with the extension line (or luer) and the adhesive sides are folded over on themselves. In some embodiments, the tags can be removed or exchanged by pulling in a direction perpendicular to the perforated line such that the tag readily tears at the perforation and can be discarded are placed in a patient's records.

An "antimicrobial agent" is defined herein as an agent that has antibiotic properties against bacteria, fungi, viruses and other pathogens and includes antibacterial agents, antifungal agents, antiviral agents and antiseptic agents.

As used herein, the term "antifungal agent" is defined as a compound having either a fungicidal or fungistatic effect upon fungi contacted by the compound. As used herein, the term "fungicidal" is defined to mean having a destructive killing action upon fungi. As used herein, the term "fungistatic" is defined to mean having an inhibiting action upon the growth of fungi.

As used herein, the term "antibacterial agent" is defined as a compound having either a bactericidal or bacteriostatic effect upon bacteria contacted by the compound. As used herein, the term "bactericidal" is defined to mean having a destructive killing action upon bacteria. As used herein, the term "bacteriostatic" is defined to mean having an inhibiting action upon the growth of bacteria.

As used herein, the term "antiviral agent" is defined as a compound that can either kill viral agents or one that stops the replication of viruses upon contact by the compound.

For the purposes of this disclosure, the phrase "effective amount" or "therapeutically effective amount" is defined as a dosage sufficient to induce a microbicidal or microbistatic effect upon the microbes contacted by the composition on a surface.

As used herein the terms "contact", "contacted", and "contacting", or "exposed" and "exposure" are used to describe the process by which any of the antimicrobial compositions disclosed in the present invention, comes in contact with or direct juxtaposition with a surface of a medical device or any other surface from which microbial growth is to be reduced or eradicated.

As used herein in the specification, "a" or "an" may mean one or more. As used herein in the claim(s), when used in conjunction with the word "comprising", the words "a" or "an" may mean one or more than one. As used herein "another" may mean at least a second or more.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

The present invention provides, in various aspects, improved antimicrobial solutions, such as improved antimicrobial catheter lock solutions. In some embodiments, an antimicrobial catheter lock solution contains an antibiotic, a chelator, and an alcohol, wherein the solution is adjusted to a pH of about 6-8. In some embodiments, the antibiotic is minocycline and/or trimethoprim, the chelator is EDTA, and the alcohol is ethanol. For example, the antimicrobial solution or catheter lock solution may contain about 3% EDTA, about 25% ethanol, and about 0.1% minocycline. In some embodiments, the antimicrobial solution or catheter lock solution may exhibit potency against biofilm, little or no toxic side effects, and blood anticoagulant properties in a human patient.

In addition to use with catheters (e.g., as a catheter lock solution or a catheter flush solution), an antimicrobial composition or solution of the present invention may be applied to or used with a medical device. The medical device may be, e.g., an endotracheal tube, a nephrostomy tube, a biliary stent, an orthopedic device, a valve, a prosthetic valve, a drainage tube, a drain, a shunt, a staple, a clip, a mesh, a film, a blood exchanging device, a port, a cardiovascular device, a defibrillator, a pacemaker lead, a wire coating, an ocular implant, an auditory implant, a cochlear implant, a dental implant, a stimulator, a drug delivery depot, a filter, a membrane, a vascular access port, a stent, an envelope, a bag, a sleeve, intravenous or other tubing, a bag, a dressing, a patch, a fiber, a pin, a vascular graft, a suture, a cardiovascular suture, or an implantable prosthesis. In some embodiments, the medical device is a catheter such as, e.g., a vascular catheter, a urinary catheter, an intracranial catheter, an intraspinal catheter, a peritoneal catheter, a central nervous system catheter, a cardiovascular catheter, a drainage catheter, a soaker catheter, an aspirating catheter, an intrathecal catheter, a neural catheter, a stimulating catheter, or an epidural catheter. The catheter may be a vascular catheter such as, e.g., a central venous catheter, an arterial line, an pulmonary artery catheter, a peripheral venous catheter, an intravenous catheter, or an intraarterial catheter.

Antimicrobial Agents and Microbes

Antimicrobial compositions of the present invention may be used to kill, destroy, or reduce the proliferation of a variety of microbes. Some non-limiting exemplary bacterial and fungal microbes that can be reduced or eradicated by the compositions and methods of the invention include *Staphylococcus* species (such as *Staphylococcus epidermidis*), *Staphylococcus aureus*; *Aspergillus* species (such as *Aspergillus flavus, Aspergillus terreus*), *Enterrococcus faecalis, Pseudomonas aeruginosa, Escherichia coli, Fusarium oxysporum*, and *Candida* species (such as *Candida krusei, Candida parapsilosis, Candida tropicalis, Candida albicans* and *Candida glabrata*).

Chelators

In some preferred embodiments of the present invention, an antimicrobial solution (e.g., a catheter lock or flush solution) comprises both a $C_{1-4}$ alcohol and a chelator such as EDTA. Chelators can bind a metal ion, typically involving the central metal ion attached by coordinate links to two or more nonmetal atoms in the same molecule. Heterocyclic rings are typically formed during chelation, with the metal atom as part of the ring. The molecule comprising the nonmetal linking atoms is termed a chelator. Chelators are used in various chemical applications, for example as titrating agents or as metal ion scavengers. Chelators can also be used to remove ions from participation in biological reactions. For example, the well-known chelator ethylenediamine-N,N,N',N',-tetraacetic acid (EDTA) can act as an anticoagulant because it is capable of scavenging ions such as calcium ions from the blood. EDTA may sequester metal ions such as $Ca^{2+}$ or $Fe^{3+}$. EDTA can also act as an antimicrobial agent, e.g., by binding iron and/or trace metals that may be important or essential for the microbes to grow and reproduce.

In some embodiments, the EDTA is present in an antimicrobial solution or composition of the present invention (e.g., in a catheter lock solution) at a concentration of from about 1-5%, 1.5-5%, 1-3.5%, 1-3%, or about 1, 1.5, 2, 2.5, 3, 3.5, 4, 4.5, or 5%, or any range derivable therein.

A variety of forms of EDTA may be used in various embodiments of the present invention. For example, the EDTA may be: EDTA free (Ethylenediamine-N,N,N',N',-tetraacetic acid), EDTA 2Na (Ethylenediamine-N,N,N',N',-tetraacetic acid, disodium salt), dihydrate EDTA 3Na (Ethylenediamine-N,N,N',N',-tetraacetic acid, trisodium salt, trihydrate), EDTA 4Na (Ethylenediamine-N,N,N',N'-tetraacetic acid, tetrasodium salt), tetrahydrate EDTA 2K Ethylenediamine-N,N,N',N'-tetraacetic acid, dipotassium salt), dihydrate EDTA 2Li (Ethylenediamine-N,N,N',N'-tetraacetic acid, dilithium salt), monohydrate EDTA ($2NH_4$ Ethylenediamine-N,N,N',N'-tetraacetic acid, diammonium salt), EDTA 3K (Ethylenediamine-N,N,N',N'-tetraacetic acid, tripotassium salt), dihydrate Ba(II)-EDTA (Ethylenediamine-N,N,N',N'-tetraacetic acid, barium chelate), Ca(II)-EDTA (Ethylenediamine-N,N,N',N'-tetraacetic acid, calcium chelate), Ce(III)-EDTA (Ethylenediamine-N,N,N',N'-tetraacetic acid, cerium chelate), Co(II)-EDTA (Ethylenediamine-N,N,N',N'-tetraacetic acid, cobalt chelate), Cu(II)-EDTA (Ethylenediamine-N,N,N',N'-tetraacetic acid, copper chelate), Dy(III)-EDTA (Ethylenediamine-N,N,N',N'-tetraacetic acid, dysprosium chelate), Eu(III)-EDTA (Ethylenediamine-N,N,N',N'-tetraacetic acid, europium chelate), Fe(III)-EDTA (Ethylenediamine-N,N,N',N'-tetraacetic acid, iron chelate), In(III)-EDTA (Ethylenediamine-N,N,N',N'-tetraacetic acid, indium chelate), La(III)-EDTA (Ethylenediamine-N,N,N',N'-tetraacetic acid, lanthanum chelate), Mg(II)-EDTA (Ethylenediamine-N,N,N',N'-tetraacetic acid, magnesium chelate), Mn(II)-EDTA (Ethylenediamine-N,N,N',N'-tetraacetic acid, manganese chelate), Ni(II)-EDTA (Ethylenediamine-N,N,N',N'-tetraacetic acid, nickel chelate), Sm(III)-EDTA (Ethylenediamine-N,N,N',N'-tetraacetic acid, samarium chelate), Sr(II)-EDTA (Ethylenediamine-N,N,N',N'-tetraacetic acid, strontium chelate). Zn(II)-EDTA (Ethylenediamine-N,N,N',N'-tetraacetic acid, zinc chelate), CyDTA (trans-1,2-Diaminocyclohexane-N,N,N',N'-tetraacetic acid, monohydrate), EDTA-OH (N-(2-Hydroxyethyl)ethylenediamine-N,N',N'-triacetic acid), or Methyl-EDTA (1,2-Diaminopropane-N,N,N',N'-tetraacetic acid). In some embodiments, the antimicrobial solution or composition may further comprise DHEG (N,N-Bis(2-hydroxyethyl)glycine), DTPA-OH (1,3-Diamino-2-hydroxypropane-N,N,N',N'-tetraacetic acid), DTPA (1,3-Diaminopropane-N,N,N',N'-tetraacetic acid), EDDA (Ethylenediamine-N,N'-diacetic acid), EDDP (Ethylenediamine-N,N'-dipropionic acid dihydrochloride), EDDPO (Ethylenediamine-N,N'-bis(methylenephosphonic acid), hemihydrate), EDTPO (Ethylenediamine-N,N,N',N'-tetrakis (methylenephosponic acid)), EGTA (O,O'-bis(2-aminoethyl) ethyleneglycol-N,N,N',N'-tetraacetic acid), HBED (N,N-diacetic acid HDTA 1,6-Hexamethylenediamine-N,N,N',N'-tetraacetic acid HIDA N-(2-Hydroxyethyl)iminodiacetic acid), IDA (Iminodiacetic acid), NTA Nitrilotriacetic acid, NTP (Nitrilotripropionic acid), NTPO (Nitrilotris(methylenephosphoric acid), trisodium salt), O-Bistren (7,19,30-Trioxa-1,4,10,13,16,22,27,33-octaabicyclo [11,11,11] pentatriacontane hexahydrobromide), TTHA (Triethylenetetramine-N,N,N',N'',N''',N''''-hexaacetic acid), or EDDS (Ethylenediamine-N,N'-disuccinic acid).

In some embodiments, an antimicrobial solution of the present invention (e.g. a catheter lock solution) may include one or more additional anticoagulants. For example, the anticoagulant may be EGTA, EDTA, heparin, urokinase, streptokinase, low molecular weight heparin, enoxaparin, sodium coumarin, indanedione, anisindione, warfarin, protamine sulfate, anti-thrombin III, nitrilotriacetic acid, potassium sodium tartrate, potassium hydrogen D-tartrate, L-tartaric acid dipotassium salt, L-tartaric acid disodium salt, L-tartaric acid monosodium salt, tris(carboxymethyl) amine, warfarin, acetylsalicylic acid, ibuprofen, indomethacin, prostaglandins, sulfinpyrazone, streptokinase, urokinase, tissue plasminogen activator, coumarin, protamine sulfate, anti-thrombin III, coumadin, protein C/protein S, nicoumalone, phenprocoumon, hirudin, hirulog, or a glycosaminoglycan. Additional chelators, anticoagulants, and/or additional agents useful in the practice of the present invention may be found in U.S. Pat. No. 5,688,516, incorporated herein by reference.

Alcohols

The antimicrobial solutions of the present invention preferably comprise an alcohol, such as an antiseptic or disinfectant alcohol. In some embodiments the alcohol is a $C_{1-4}$ alcohol such as, e.g., ethanol, methanol, butanol, or isopropanol. IN some embodiments, the alcohol may be cyclohexanol, benzyl alcohol, chlorobutanol, 2-bromo-2-nitropropan-1,3-diol, or phenylethyl alcohol. In some embodiments, the final alcohol concentration is in the range of about 5%-80% (v/v), more preferably in the range of about 10% to 50%, more preferably in the range of about 15% to 40%, more preferably in the range of 20% to 30%, or 5%, 6%, 7%, 8%, 9%, 10%, 15%, 20%, 25%, 30%, 35%, 40%, 45%, 50%, 55%, 60%, 65%, 70%, 75%, or 80% (v/v), or any range derivable therein, of the alcohol in the preparation of the instant antimicrobial solutions. This includes the use of intermediate concentrations of alcohol such as 11%, 22.5%, 26% and the like. In some embodiments where the antimicrobial solution or composition may be used as a catheter lock or flush solution, it may be desirable to use a concentration of alcohol of about 30% or less such as, e.g., about 5, 10, 12.5, 15, 17.5, 20, 22.5, 25, 27.5%, less than 30%, or about 30%, or any range derivable therein.

Additional Agents

It is also contemplated that any additional pharmacologically active ingredients or sterilization agents may be comprised in the solutions of the present invention or may be used separately for flushing or treating the devices of the present invention to further reduce or eliminate pathogenic microbes and viruses. Typical pharmacologically active ingredients include antifibrin agents, anti-thrombotic agents, and anti-inflammatory agents. Anti-inflammatory agents include steroids, and nonsteroidal anti-inflammatory agents, and salicylates. Anti-thrombotic drugs including acetylsalicylic acid, dipyridamole, heparin, ibuprofen, indomethacin, prostaglandins, sulfinpyrazone, warfarin, thrombolytic enzymes such as streptokinase, urokinase, or plasminogen activator may be used. Complexing agents such as ammonium-1-pyrrolidine dithiocarbanate may also be used. However, the above examples are not meant to be limiting. In some embodiments, an antimicrobial solution or a catheter lock solution may comprise one or more additional anticoagulant and/or an anti-inflammatory agent.

Pharmaceutical compositions such as an antimicrobial solution or catheter lock solution, as described herein, may contain an additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. An antimicrobial solution or catheter lock solution as described herein may contain an additional active ingredient, e.g., as exemplified by *Remington: The Science and Practice of Pharmacy, 21st Ed.*, Lippincott Williams and Wilkins, 2005, incorporated herein by reference. Moreover, for animal (e.g., human) administration, it will be understood that preparations should typically meet sterility, pyrogenicity, general safety and purity standards as required by FDA Office of Biological Standards.

Packaging and Kits

Various packaging techniques may be employed in providing an antimicrobial solution or catheter lock or flush solution of the invention as part of a commercially available kit. The kit will optionally include an instruction sheet insert to identify how the kit is to be used.

In some embodiments, the antimicrobial solution comprises minocycline as the antibiotic, EDTA as the chelator/anticoagulant, and ethanol. However, as will be appreciated by the skilled artisan, any other combination of one or more antibiotic, one or more chelator/anticoagulant, and ethanol as described in the present disclosure may be packaged in a similar manner. The kit may comprise of one or two or three or more compartments. The components of the kit may be provided in separate compartments or in the same compartment. The components of the kit may be provided separately or mixed. The mixed components may contain two or more agents such as an antibiotic, a chelator/anticoagulant, or ethanol, or additional component.

In some embodiments, the kit comprises (i) an antibiotic in a first container; (ii) a solution containing an EDTA and an alcohol at a pH of about 6-8 in in a second container; (iii) a suitable connector for mixing the antibiotic and the solution; and (iv) a suitable syringe or container for administering the mixed solution, e.g., to a catheter. Alternately, the ETDA and the alcohol may be present in separate containers, such that the pH or each of the separate containers or the pH of the resulting mixed solution is about 6-8. The antibiotic (e.g., minocycline) and/or EDTA may be lyophilized or dry. For example, 3-9 mg minocycline (dry), 10-100 mg EDTA (powdered) and one wet component comprising 3 ml diluent (alcohol or diluted in saline or distilled water) at a pH sufficient to achieve a pH of about 6-8. When ready for use, the dry components, minocycline and EDTA, will be allowed to mix with the diluent. In some embodiments, a WET/WET dual chamber container system, available from Becton-Dickinson, may be used in these applications.

Each container of the kits will generally include at least one vial, test tube, flask, bottle, syringe or other container, into which the antibiotic, EDTA, and/or alcohol may be placed or suitably aliquoted. In some embodiments, the kit may comprise a suitable syringe or container for administering the mixed solution to a catheter.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Observed Precipitation in Antimicrobial Solutions

When combining 25% ethanol with pure, single EDTA sodium salts (e.g., as described in U.S. Pat. No. 7,601,731), the inventors observed either pH or solubility issues. 25% ethanol+3% pure tetrasodium EDTA yields a pH of 10.9. This pH may be harmful to blood vessels, can induce clot formation and destabilize Minocycline.

The inventors have found that at 25% ethanol+3% pure disodium EDTA solutions yields a pH of 4.75. The inventors observed that, within hours, a precipitate forms. In the presence of 0.1% Minocycline the precipitate was observed to still form. This precipitate can be undesirable in a catheter lock or flush because the precipitate can clog catheter lumens or create emboli. Monosodium EDTA is difficult to source commercially but is expected to produce a pH below disodium EDTA. The inventors further observed that pure tetra-acid EDTA is mostly insoluble in water/ethanol which is undesirable for the reasons enumerated above and additionally, yields a pH of 3.1 which is harmful to blood vessels and destabilizing to Minocycline. Disodium EDTA is a commonly used EDTA salt in blood contacting applications because it is water soluble and has better calcium binding capacity than tetrasodium EDTA. However, it still produces an acidic pH and one still needs to overcome a precipitation problem with disodium EDTA in the presence of 25% ethanol.

To overcome the precipitation problem with 25% Ethanol/3% disodium EDTA/0.1% Minocycline, the inventors surprisingly observed that adjustment to pH greater than 5.5 substantially prolongs stability (minimizes precipitation) without the need to reduce EDTA concentration or form novel grafted chelator chemicals. Excessively basic pH (pH>8.5) can be detrimental to clotting and endothelial health. The pH adjustment to 6-8 range may be used in the Minocycline/EDTA/Ethanol system.

Example 2

Procedure for Preparing 0.1% Minocycline, 3% Disodium EDTA, 25% Ethanol Lock

A 0.1% Minocycline, 3% disodium EDTA, 25% Ethanol catheter lock solution was made as follows:
1. Weigh out 660 mg disodium EDTA powder, and dissolve in 11 mL sterile water in a sterile vessel. Shake EDTA and sterile water until completely dissolved. Resulting concentration is 60 mg/mL. Filter with 0.22 micron filter into an empty sterile 30 mL vial to a filtrate volume of 10 mL.
2. Reconstitute a 100 mg vial of minocycline with 10 mL sterile water using a sterile syringe, and withdraw 2 mL (20 mg). Add to the vial with the EDTA.
3. Using a sterile syringe, draw up 5 mL of alcohol, and add to the vial with the EDTA and minocycline
4. QS to total volume of 20 ml with water, representing EDTA 30 mg, minocycline 1 mg, and alcohol 25% per 1 ml.
5. Prepare 19 syringes with 1 mL in each syringe. (3 mL sterile syringes can be used).
6. Label the syringes, and store protected from light.

Example 3 pH Measurement and Stability Observations with Storage at 4° C.

A consistent pH of 4.5±0.1 was recorded for the samples prepared as described in Example 1. Nine of the pH 4.5 Minocycline/EDTA/Ethanol syringes were stored at 25° C. and observed daily for precipitation by removing and rotating the syringes (N indicates NO precipitate observed, Y indicates precipitate observed):

| Syringe # | Baseline (0 hrs) | Day 1 (24 hrs) | Day 2 (48 hrs) | Day 3 (72 hrs) |
| --- | --- | --- | --- | --- |
| 1 | N | Y | Y | Y |
| 2 | N | Y | Y | Y |
| 3 | N | Y | Y | Y |
| 4 | N | Y | Y | Y |
| 5 | N | Y | Y | Y |
| 6 | N | Y | Y | Y |
| 7 | N | Y | Y | Y |
| 8 | N | Y | Y | Y |
| 9 | N | Y | Y | Y |
| | 0/9 = 0% | 9/9 = 100% | 9/9 = 100% | 9/9 = 100% |

All (100%) of the samples precipitated within 24 hours when stored at 25° C.

Example 4

Stability Observations with Storage at 4° C.

Nine of the pH 4.5 Minocycline/EDTA/Ethanol syringes were stored at 4° C. and observed daily for precipitation by removing and rotating the syringes and by observing through a magnifying glass (N indicates NO precipitate observed, Y indicates precipitate observed):

| Syringe # | Baseline (0 hrs) | Day 1 (24 hrs) | Day 2 (48 hrs) | Day 3 (72 hrs) |
|---|---|---|---|---|
| 1 | N | Y | Y | Y |
| 2 | N | Y | Y | Y |
| 3 | N | Y | Y | Y |
| 4 | N | Y | Y | Y |
| 5 | N | Y | Y | Y |
| 6 | N | Y | Y | Y |
| 7 | N | Y | Y | Y |
| 8 | N | Y | Y | Y |
| 9 | N | Y | Y | Y |
| | 0/9 = 0% | 9/9 = 100% | 9/9 = 100% | 9/9 = 100% |

All (100%) of the samples precipitated within 24 hours when stored at 4° C.

Example 5

Procedure for pH Adjusted Disodium EDTA Using Base

A solution containing disodium EDTA that was pH adjusted using base was prepare by the following method:
1. Weigh out 300 mg disodium EDTA powder in 30 ml vial, and dissolve in 9.3 mL sterile water. Shake EDTA and sterile water until completely dissolved. QS to 10 ml with water. Resulting concentration is 30 mg/mL (3%).
2. Measure pH, Add 1M NaOH recording volume added and remeasure pH.

| Volume 3% disodium EDTA | Total Volume 1M NaOH added | pH |
|---|---|---|
| 10 ml | 0 | 4.5 |
| | 0.5 ml | 4.9 |
| | 1.0 ml | 5.4 |
| | 1.5 ml | 6.9 |
| | 1.7 ml | 7.4 |

Example 6

Procedure for pH Adjusted Tetrasodium EDTA Using Disodium EDTA

A solution containing tetrasodium EDTA pH adjusted with disodium EDTA was prepared by the following method:
1. Weigh out 300 mg disodium EDTA powder in 30 ml vial, and dissolve in 9.3 mL sterile water. Shake EDTA and sterile water until completely dissolved. QS to 10 ml with water. Resulting concentration is 30 mg/mL (3%).
2. Weigh out 300 mg tetrasodium EDTA powder in 30 ml vial, and dissolve in 9.3 mL sterile water. Shake EDTA and sterile water until completely dissolved. QS to 10 ml with water. Resulting concentration is 30 mg/mL (3%).
3. Measure pH of tetrasodium EDTA and add disodium EDTA recording volume added and pH after each addition The following solutions were produced:

| Total volume 3% tetrasodium EDTA added | Total volume 3% disodium EDTA added | pH |
|---|---|---|
| 5 ml | 0 | 10.9 |
| | 1 ml | 10.2 |
| | 2 ml | 9.5 |
| | 3 ml | 9.0 |
| | 4 ml | 8.8 |
| | 5 ml | 8.1 |
| | 6 ml | 7.1 |

Example 7

Consistency of pH Adjustment of Minocycline/Disodium EDTA/Ethanol Using 1 M Sodium Hydroxide The consistency of pH adjustment of a minocycline/disodium EDTA/Ethanol solution was evaluated using 1 M sodium hydroxide, as follows:
1. Weigh out 660 mg disodium EDTA powder, and dissolve in 9.3 mL sterile water in a sterile vessel. Shake EDTA and sterile water for 10 minutes. It will completely dissolve but it takes a while. Resulting concentration is 60 mg/mL.
2. add 1.7 mL of 1M NaOH to the disodium EDTA solution.
3. Filter with 0.22 micron filter into an empty sterile 30 mL vial to a volume of 10 mL.
4. Reconstitute a 100 mg vial of minocycline with 10 mL sterile water using a sterile syringe, and withdraw 2 mL (20 mg). Add to the vial with the EDTA.
5. Using a sterile syringe, draw up 5 mL of alcohol, and add to the vial with the EDTA and minocycline.
6. QS to total volume of 20 ml with water, representing EDTA 30 mg, minocycline 1 mg, and alcohol 25% per 1 ml.
7. Prepare 19 syringes with 1 mL in each syringe. (1-3 mL sterile syringe can be used) Label the syringes and protect from light.

The pH from seven syringes, sampled randomly, were measured using a pH meter. The following results were observed:

| Syringe # | pH final solution |
|---|---|
| 1 | 7.29 |
| 2 | 7.30 |
| 3 | 7.27 |
| 4 | 7.26 |
| 5 | 7.30 |
| 6 | 7.31 |
| 7 | 7.29 |
| Average pH | 7.29 |
| Standard deviation | 0.02 |

Example 8

Observation of Stability of Samples Prepared in Example 6

Nine syringes from the samples prepared in Example 6 were stored at 25° C. and observed daily for precipitate formation by rotating them and by observing through a magnifying glass (N indicates No precipitate observed; Y indicates a precipitate was observed):

| Syringe # | Baseline (0 hrs) | Day 1 (24 hrs) | Day 2 (48 hrs) | Day 3 (72 hrs) |
|---|---|---|---|---|
| 1 | N | N | N | N |
| 2 | N | N | N | N |
| 3 | N | N | N | N |
| 4 | N | N | N | N |
| 5 | N | N | N | N |
| 6 | N | N | N | N |
| 7 | N | N | N | N |
| 8 | N | N | N | N |
| 9 | N | N | N | N |
|  | 0/9 = 0% | 0/9 = 0% | 0/9 = 0% | 0/9 = 0% |

Example 9

Observation of Stability of Samples Prepared as in Example 6 at 4° C. and 25° C.

Sample preparation described in Example 6 was repeated. Nine syringes were stored at 25° C. and 9 at 4° C. The syringes were observed daily for precipitate formation by rotating them and by observing through a magnifying glass (N indicates No precipitate observed; Y indicates a precipitate was observed):

| 4 C storage Syringe # | Baseline (0 hrs) | Day 1 (24 hrs) | Day 2 (48 hrs) | Day 3 (72 hrs) |
|---|---|---|---|---|
| 1 | N | N | N | N |
| 2 | N | N | N | N |
| 3 | N | N | N | N |
| 4 | N | N | N | N |
| 5 | N | N | N | N |
| 6 | N | N | N | N |
| 7 | N | N | N | N |
| 8 | N | N | N | N |
| 9 | N | N | N | N |
|  | 0/9 = 0% | 0/9 = 0% | 0/9 = 0% | 0/9 = 0% |

| 25 C storage Syringe # | Baseline (0 hrs) | Day 1 (24 hrs) | Day 2 (48 hrs) | Day 3 (72 hrs) |
|---|---|---|---|---|
| 1 | N | N | N | N |
| 2 | N | N | N | N |
| 3 | N | N | N | N |
| 4 | N | N | N | N |
| 5 | N | N | N | N |
| 6 | N | N | N | N |
| 7 | N | N | N | N |
| 8 | N | N | N | N |
| 9 | N | N | N | N |
|  | 0/9 = 0% | 0/9 = 0% | 0/9 = 0% | 0/9 = 0% |

As shown above, solutions of Minocycline (1 mg/ml), 3% EDTA, and 25% Ethanol were observed to be much more shelf-stable at pH 6-8 than at more acidic pHs.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 7,601,731
U.S. Pat. No. 8,541,472
U.S. Pat. No. 5,362,754
U.S. Pat. No. 5,688,516
U.S. Pat. No. 6,350,251
WO2012/167368
EP1245247
Harris, D C. EDTA Titrations. Chap 11 in Quantitative Chemical Analysis $8^{th}$ edition. WH Freeman and Co, NY N.Y. 2010
Kluger et al., In: Interscience Conference on Antimicrobial Agents and Chemotherapy (ICAAC) Abstracts of the 39th Meeting, 514, 1999.
Maki et al., In: Hospital Infections. Bennett J V, Brachman P S, eds. Lippincott-Raven, Philadelphia, Pa., pp 689-94, 1998.
Raad et al., J. Infect. Dis. 168:400-407, 1993.
Raad et al., Antimicrob. Agents Chemother., 46(2):327-332, 2002.
Raad et al., Arch. Intern. Med. 162:871-878, 2002.
Remington: The Science and Practice of Pharmacy, $21^{st}$ Ed., Lippincott Williams and Wilkins, 2005
Sheretz et al., "In vitro efficacy of minocyline (M)/EDTA (MEDTA) as a catheter lock solution," Shea Merck Healthcare Epidemiology Search Abstracts, 2002.

What is claimed is:

1. A pharmaceutically acceptable antimicrobial solution comprising:
   (i) a $C_{1-4}$ alcohol;
   (ii) EDTA or a salt thereof; and
   (iii) an antibiotic;
   wherein said solution has a pH of about 6-8, and wherein said solution comprises a pharmaceutically acceptable excipient or diluent;
   wherein the $C_{1-4}$ alcohol is ethanol, isopropanol, or butanol; and
   wherein the antibiotic is a tetracycline or trimethoprim.

2. The solution of claim 1, wherein the antibiotic is trimethoprim or minocycline.

3. The solution of claim 1, wherein the $C_{1-4}$ alcohol is ethanol.

4. The solution of claim 1, wherein the $C_{1-4}$ alcohol is present in the solution at a concentration of about 10-40%.

5. The solution of claim 1, wherein the solution comprises about 1-5% EDTA.

6. The solution of claim 1, wherein the EDTA is an acidic EDTA, and wherein the solution further comprises a base.

7. The solution of claim 6, wherein the acidic EDTA is EDTA free acid, EDTA 2Na, EDTA 2K, EDTA diammonium, or a diacid of EDTA.

8. The solution of claim 6, wherein the base is sodium hydroxide, potassium hydroxide, ammonia, an amine, or urea.

9. The solution of claim 1, wherein the EDTA is a basic EDTA, and wherein the solution further comprises an acid.

10. The solution of claim 9, wherein the basic EDTA is EDTA 4Na, EDTA 4K, or tetra ammonium EDTA.

11. The solution of claim 9, wherein the acid is hydrochloric acid or acetic acid.

12. The solution of claim 1, wherein the solution comprises both an acidic EDTA and a basic EDTA.

13. The solution of claim 1, wherein the solution comprises a pharmaceutically acceptable saline diluent.

14. The solution of claim 1, wherein the solution has a pH of about 6.5-7.5.

15. The solution of claim 1, wherein the solution further comprises polyethylene glycol.

16. The solution of claim 1, wherein the solution comprises a saline diluent, wherein the solution has a pH of about 6.5-7.5, and wherein the solution is further defined as a catheter lock solution.

17. A medical device locking solution comprising or consisting of a solution of claim 1.

18. A kit comprising:
 (i) an antibiotic in a first container, wherein the antibiotic is a tetracycline or trimethoprim;
 (ii) a solution containing EDTA or a salt thereof and an alcohol at a pH of about 6-8 in in a second container, wherein the alcohol is ethanol, isopropanol, or butanol;
 (iii) a suitable connector for mixing the antibiotic and the solution; and
 (iv) a suitable syringe or container for administering the mixed solution to a catheter.

19. A method of flushing or locking a catheter in a subject, comprising administering the solution of claim 1 to the catheter in the subject.

20. The solution of claim 1, wherein the tetracycline is minocycline.

21. The method of claim 19, wherein the catheter is an intravascular catheter, a urinary catheter, a brain catheter, a nephrostomy tube, or a drain or drainage catheter.

22. The method of claim 21, wherein the subject is a human.

23. The solution of claim 1, wherein the solution comprises a saline diluent, wherein the solution has a pH of about 6.5-7.5, and wherein the solution is comprised in a syringe or vial.

24. The kit of claim 18, wherein one or more labels or removable extension-line tags is attached to the catheter.

25. The kit of claim 24, wherein the tags are symmetric peel-off tags comprising adhesive on one side and pre-perforated lines on about the mid-section or the tags.

26. The kit of claim 18, wherein the antibiotic is lyophilized.

27. The kit of claim 18, wherein the alcohol is ethanol.

28. The kit of claim 18, wherein the first container is a vial or syringe, and wherein the second container is a vial or syringe.

29. The kit of claim 18, wherein the antibiotic is a lyophilized antibiotic, and wherein the first container and the second container are each a vial or syringe.

30. The solution of claim 7, wherein the acidic EDTA is EDTA 2Na (disodium EDTA).

* * * * *